United States Patent
Shida et al.

(10) Patent No.: US 6,829,325 B2
(45) Date of Patent: Dec. 7, 2004

(54) X-RAY CT APPARATUS AND PROCESSING METHOD THEREFOR

(75) Inventors: Koichi Shida, Tokyo (JP); Naoyuki Kawachi, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 210 days.

(21) Appl. No.: 10/319,354

(22) Filed: Dec. 13, 2002

(65) Prior Publication Data

US 2003/0118146 A1 Jun. 26, 2003

(30) Foreign Application Priority Data

Dec. 26, 2001 (JP) ........................................ 2001-394409

(51) Int. Cl.⁷ ................................................. A61B 6/03
(52) U.S. Cl. ........................................... 378/4; 378/901
(58) Field of Search ............................ 378/4, 8, 15, 19, 378/901

(56) References Cited

U.S. PATENT DOCUMENTS

| | | | |
|---|---|---|---|
| 5,748,697 A | 5/1998 | Tam | |
| 6,115,487 A | 9/2000 | Toth et al. | |
| 6,324,243 B1 | 11/2001 | Edic et al. | |
| 6,324,247 B1 * | 11/2001 | Besson | 378/15 |
| 6,463,118 B2 | 10/2002 | Besson | |
| 6,597,803 B1 * | 7/2003 | Pan et al. | 382/131 |
| 2003/0123718 A1 * | 7/2003 | Edic et al. | 382/131 |

* cited by examiner

Primary Examiner—David V Bruce
(74) Attorney, Agent, or Firm—Carl B. Horton, Esq.; Armstrong Teasdale LLP

(57) ABSTRACT

With the object of improving image quality while keeping short the time taken to reconstruct the first X-ray tomogram at the time of start of scanning in its real-time display mode, an X-ray CT apparatus having a rotary unit for causing an X-ray source and an X-ray detector for detecting X-rays from the X-ray source to rotate integrally around a subject, is provided with a full data reconstructing device for reconstructing tomograms on the basis of penetrating X-ray data of each view detected during a full turn around the subject, a segment data reconstructing device for reconstructing tomograms on the basis of penetrating X-ray data of each view detected during a turn by (180+α) degrees, and a change-over device for counting the tomograms reconstructed after the start of scanning, and changing over between the full data reconstructing device and segment data reconstructing device according to the count.

31 Claims, 15 Drawing Sheets

FIG. 14B
Segment Weighting Table 1.0

Channel

| Data 1-0 | Data 1-1 | Data 1-2 | Data 1-3 | ... | Data 1-39 | Data 1-40 | ... | Data 1-239 | Data 1-240 | ... | Data 1-359 |
| Data 2-0 | Data 2-1 | Data 2-2 | Data 2-3 | ... | Data 2-39 | Data 2-40 | ... | Data 2-239 | Data 2-240 | ... | Data 2-359 |
| Data 3-0 | Data 3-1 | Data 3-2 | Data 3-3 | ... | Data 3-39 | Data 3-40 | ... | Data 3-239 | Data 3-240 | ... | Data 3-359 |
| ⋮ | | | | | | | | | | | |
| Data 999-0 | Data 999-1 | Data 999-2 | Data 999-3 | ... | Data 999-39 | Data 999-40 | ... | Data 999-239 | Data 999-240 | ... | Data 999-359 |
| Data 1000-0 | Data 1000-1 | Data 1000-2 | Data 1000-3 | ... | Data 1000-39 | Data 1000-40 | ... | Data 1000-239 | Data 1000-240 | ... | Data 1000-359 |

View

360

X-RAY CT APPARATUS AND PROCESSING METHOD THEREFOR

CROSS REFERENCE TO RELATED APPLICATIONS

This application claims the benefit of Japanese Application No. 2001-394409 filed Dec. 26, 2001.

BACKGROUND OF THE INVENTION

The present invention relates to an X-ray CT (computerized tomography) apparatus for obtaining tomograms of the subject by X-ray irradiation.

An X-ray CT apparatus irradiates the subject (patient) with X-rays to detect differences in X-ray absorption rate among different tissues of the human body such as internal organs, blood and gray matter with an X-ray detector, and processes the detected differences with a computer to obtain (reconstruct) the images (X-ray tomograms) of the cut planes (planes in the respective sliced planes, i.e. sliced planes) of the photographed regions.

The X-ray CT apparatus has, available in the reconstruction of X-ray tomograms, a real-time display mode (Smart View) function in addition to a regular display mode for use in usual X-ray CT tomography, and one or the other of the two modes is selectively used according to the purpose.

The real-time display mode is for use in observing, for instance when the physician needles a patient who is the subject during axial scanning, the needled state, and allows, when the needle is moved, following the movement of the needle to update the display on a real-time basis.

The X-ray CT apparatus is provided with a segment data reconstruct processing (Segment Recon) capability as a data processing capability matching the real-time display mode. The segment data reconstruct processing takes place reconstruct X-ray tomograms on the basis of projection data obtained when a gantry provided with an X-ray tube and a detector revolves around the subject by (180+α) degrees. The "α" here is what is known as the Fan-Angle; while sufficient projection data for picking up parallel beam data for 180 degrees are needed to reconstruct X-ray tomograms, picking-up of an equivalent of α extra degrees is needed to pick up parallel beam data for 180 degrees.

Since the segment data reconstruct processing (Segment Recon) permits reconstruction of X-ray tomograms by picking up projection data for (180+α) degrees, it is made possible to reduce the time required for picking up projection data at the time of start of scanning (i.e. to reduce the time required for reconstructing the first tomogram), and accordingly this can be considered a suitable processing method for the real-time display mode.

However, since the segment data reconstruct processing (Segment Recon) which is the processing method in the real-time display mode, use only a small quantity of projection data for reconstruction, it gives only poor image quality though it takes little time for reconstruction of the X-ray tomogram of the first frame, and moreover involves the problem of giving rise to "tangent artifacts" peculiar to segment data reconstruct processing (Segment Recon) and "artifacts dependent on the tube-detector angles". Tangent artifacts are noise arising linearly at the end of each part (e.g. a bone or each internal organ) in a reconstructed X-ray tomogram.

The artifacts dependent on the tube-detector angles are visual noise arising dependent on the rotational angles of the X-ray tube and the detector relative to the subject at the time of start of scanning in picking up projection data in the segment data reconstruct processing (Segment Recon). If the sectional shape of the subject is a true circle, no artifact dependent on the tube-detector angles will arise, but, if the sectional shape of the subject is an oval for instance, the extent to which artifacts arise will vary depending on whether the scanning is start in the direction of the minor axis or that of the major axis, and such artifacts can arise only when the segment data reconstruct processing (Segment Recon) is used.

SUMMARY OF THE INVENTION

It is therefore an object of the present invention to improve the image quality and to reduce artifacts in the real-time display mode of an X-ray CT apparatus while keeping short the time taken to reconstruct the first X-ray tomogram at the time of start of scanning.

In order to solve this problem, for instance an X-ray CT apparatus according to the invention has the following configuration. Thus, the X-ray CT apparatus has a rotary unit for causing an X-ray source and an X-ray detector for detecting X-rays from the X-ray source to rotate integrally around a subject, provided with: a full data reconstructing means for reconstructing tomograms on the basis of penetrating X-ray data of each view detected during a full turn around the subject, a segment data reconstructing means for reconstructing tomograms on the basis of penetrating X-ray data of each view detected during a less than full turn around the subject in a prescribed angle of rotation, and a changeover means for counting the tomograms reconstructed after the start of scanning, and changing over between the full data reconstructing means and the segment data reconstructing means according to the count.

According to the present invention, it is possible to improve image quality and reduce artifacts while keeping short the time taken to reconstruct the first X-ray tomogram at the time of start of scanning in the real-time display mode.

Further objects and advantages of the present invention will be apparent from the following description of the preferred embodiments of the invention as illustrated in the accompanying drawings.

BRIEF DESCRIPTION OF THE DRAWINGS

FIG. 6 is diagrams showing an outline of the Fan-Para conversion processing in the first mode of implementing the invention.

FIG. 14 is diagrams showing an example of segment weighting table for use in reconstructing the second frame of X-ray tomogram by full data reconstruct processing in the X-ray CT apparatus in the second mode of implementing the invention.

DETAILED DESCRIPTION OF THE INVENTION

The present invention will be described in detail with reference to modes of carrying it out illustrated in drawings.

First Mode of Implementation

<System Configuration of X-ray CT Apparatus>

Figure 3:
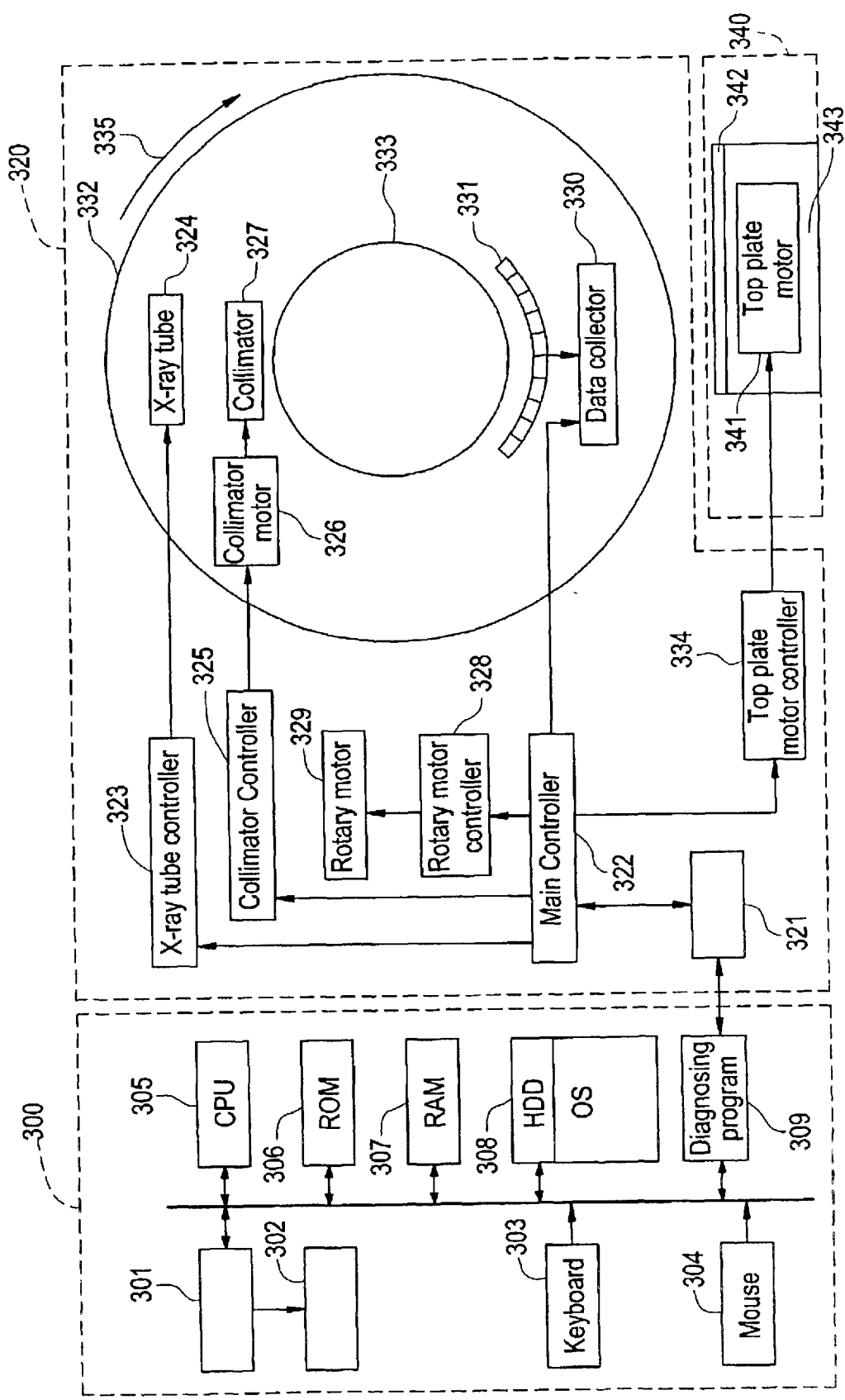
FIG. 3 is a system configuration diagram of an X-ray CT apparatus in the first mode of implementing the present invention.

FIG. 3 is a system configuration diagram of an X-ray CT apparatus in a first mode of implementing the invention.

As illustrated in FIG. 3, the X-ray CT apparatus is composed of a gantry device 320 for irradiating the subject (patient) with X-rays and detecting X-rays having penetrated the mounted subject; an operation console 300 for causing various settings to be done by transmitting instruction signals to the gantry device 320, reconstructing X-ray tomograms on the basis of projection data outputted from the gantry device 320, and displaying the reconstructed data; and a carrier 340 for mounting the subject and carrying him or her to inside the gantry device.

The gantry device denoted by 320 has the following configuration including a main controller 322 responsible for controlling the whole device.

Reference numeral 321 denotes an interface (I/F) for communicating with the operation console 300; and 332, a gantry rotating unit having inside an X-ray tube 324 (under drive control by an X-ray tube controller 323) for generating X-rays, a collimator 327 for defining the range of irradiation with X-rays, and a collimator motor 326 for adjusting the slit width which defines the range of irradiation with X-rays by the collimator 327 and adjusting the position of the Z axis (in the direction normal to the drawing) of the collimator 327. Driving of this collimator motor 326 is controlled with a collimator controller 325.

The gantry rotating unit denoted by 332 is provided with an X-ray detector 331 for detecting X-rays having penetrated the subject, and a data collector 330 for collecting projection data acquired from the X-ray detector 331. The X-ray tube 324 and the collimator 327 on one hand and the X-ray detector 331 on the other are provided in opposite positions with a void portion 333 in-between, and the gantry rotating unit 332 is rotating in the direction of an arrow 335 in a state in which that relationship is maintained. This rotation is driven by a rotary motor 329 whose rotating speed is controlled in a prescribed control period with a drive signal from a rotary motor controller 328.

The carrier 340 has a top plate 342 for actually mounting the subject and a table 343 for holding the top plate 342. The top plate 342 is driven by a top plate motor 341 in the direction of the Z axis (i.e., the carrying direction of the top plate=the Z axis direction), and rotating speed of the driving of the top plate motor 341 is whose rotating speed is controlled in a prescribed control period with a drive signal from a top plate motor controller 334.

The main controller 322 analyzes various instruction signals received via the I/F 321, and based on them outputs various control signals to the X-ray tube controller 323, the collimator controller 325, the rotary motor controller 328, the top plate motor controller 334 and the data collector 330. Also, the main controller 322 delivers projection data collected by the data collector 330 to the operation console 300 via the I/F 321.

The operation console 300 is a so-called work station and, as illustrated, has the following configuration including a CPU 305 responsible for controlling the whole device, a ROM 306 storing a boot program and the like, and a RAM 307 functioning as a main memory.

An HDD 308 is a hard disk drive, wherein there are stored an OS and a diagnosing program for giving various instruction signals to the gantry device 320 and reconstructing X-ray tomograms on the basis of projection data received from the gantry device 320. A VRAM 301 is a memory for developing image data to be displayed, and developing image data and the like here makes it possible to display them on a CRT 302. Reference numerals 303 and 304 respectively denote a keyboard and a mouse for doing various settings. Further, 309 refers to an interface for communicating with the gantry device 320.

<Outline of Reconstruct Processing>

Figure 4:
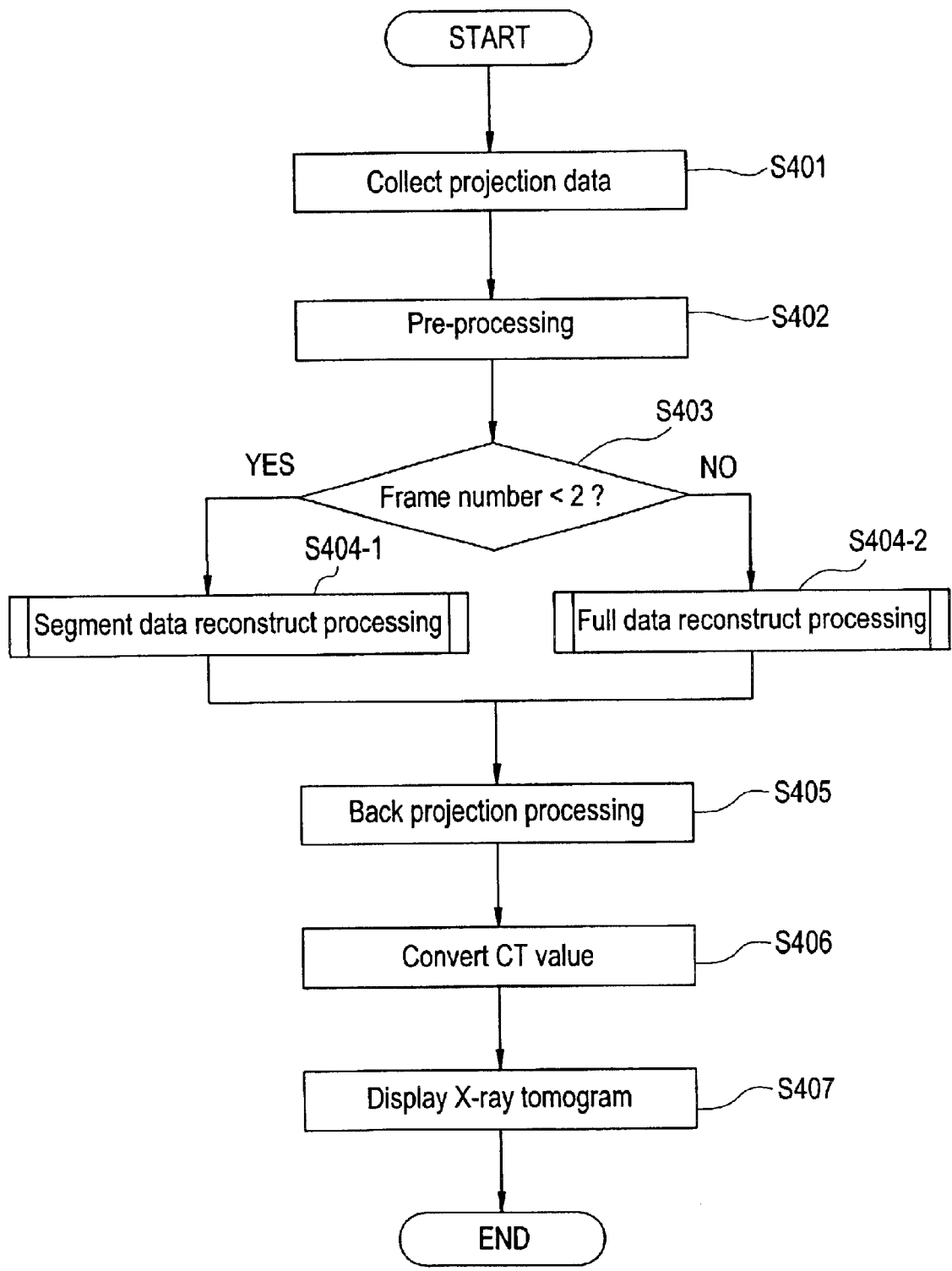
FIG. 4 is a chart showing the flow of processing to reconstruct X-ray tomograms in the diagnosing program stored in the X-ray CT apparatus in the first mode of implementing the invention.

FIG. 4 is a chart showing the flow of processing to reconstruct X-ray tomograms in the diagnosing program stored in the HDD 308 of the X-ray CT apparatus in the first mode of implementing the present invention.

First scan processing is performed to acquire projection data (step S401). At step S402 are performed various pre-processing operations including logarithmic conversion and offset compensations to compensate the characteristics of detecting elements which the X-ray detector 331 is provided with.

Then at step S403, it is judged whether the frame of X-ray tomogram to be reconstructed is the first frame X-ray tomogram (i.e., whether or not the number of frames is less than two) or the second or any subsequent X-ray tomogram.

If the number of frames is less than two, the flow will go ahead to step S404-1 to perform segment data reconstruct processing or, if the number of frames is two or more, it will move ahead to step S404-2 to perform full data reconstruct processing. Details of the segment data reconstruct processing and the full data reconstruct processing will be described with reference to FIG. 5 through FIG. 8.

Next, after back projection processing is performed at step S405, CT values are converted into data of about 256 gradations according to the window level and the window width (step S406), and an X-ray tomogram is outputted for display on a monitor such as a CRT X-ray tomogram (step S407).

<Details of Segment Data Reconstruct Processing>

Figure 1A:
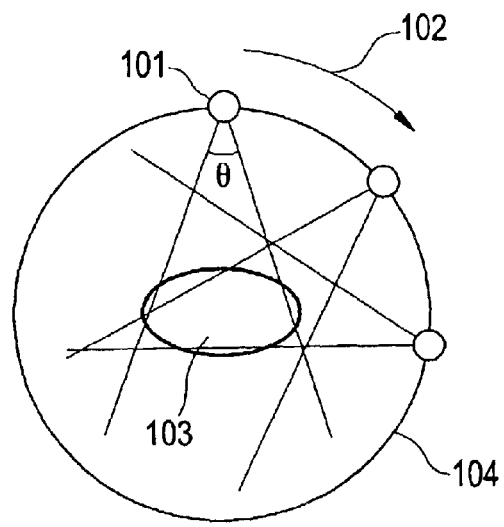
FIG. 1 is conceptual diagrams plainly representing the function of the segment data reconstruct processing mode in a usual X-ray CT apparatus.
Figure 1B:
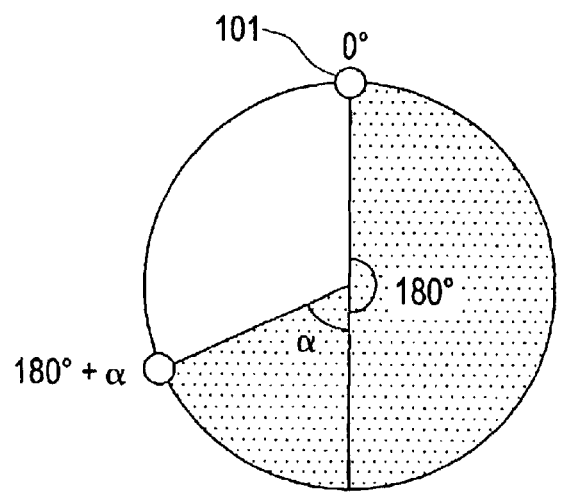
Figure 1C:
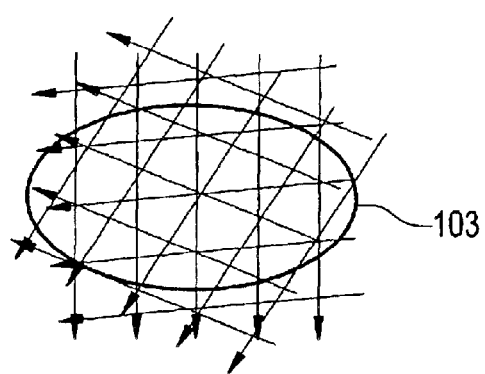

FIG. 1 are conceptual diagrams plainly representing the function of segment data reconstruct processing (Segment Recon). In FIG. 1(A), reference numeral 101 denotes an X-ray tube which, while revolving around a subject 103 along a locus denoted by 104 in the direction of an arrow 102, irradiates the subject 103 with X-rays at prescribed irradiation angle θ. FIG. 1(B) illustrates the movement of the X-ray tube during the segment data reconstruct processing until the first (frame of) X-ray tomogram is reconstructed at the time of start of scanning. Irradiation with X-rays and detection with the detector are started at the position of 0 degree in the diagram and, when the tube has rotated to the position of (180+α) degrees, the first frame of X-ray tomogram is acquired. FIG. 1(C) shows the penetration paths (indicated by arrows in the diagram) of the X-rays penetrating the subject 103 during the rotation of the X-ray tube by (180+α) degrees. A rotation by (180+α) degrees gives parallel beams for 180 degrees.

Figure 5:
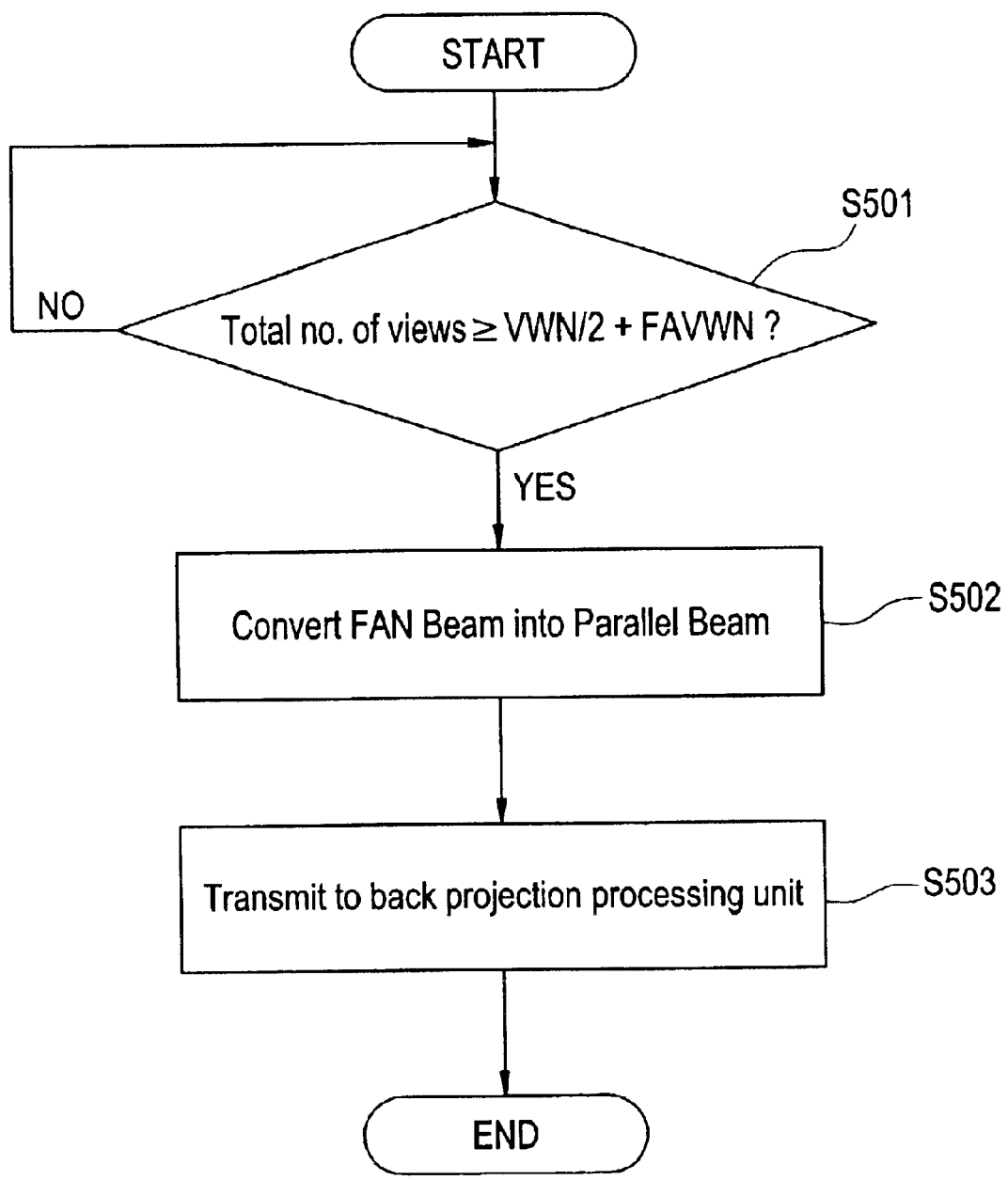
FIG. 5 is a chart showing details of the segment data reconstruct processing in the X-ray CT apparatus in the first mode of implementing the invention.

FIG. 5 shows details of the segment data reconstruct processing at step S404-1 mentioned above. The term "View" in the chart refers to picking-up of projection data by the X-ray detector 331 at any desired angle, and the "total number of Views", to the number of times projection data have been picked up since the start of scanning (i.e. the number of Views). "VWN" refers to the number of Views picked up during a full turn of the gantry rotating unit 332 around the subject, and "FAVWN", that of Views picked up during a turn of the gantry rotating unit 332 by a fan angle of α degrees (hence, FAVWN=VWN×α/360). The values of VWN and FAVWN are predetermined for each X-ray CT apparatus.

At step S501, the total number of Views since the start of scanning is counted. If the total number of Views has reached ≦(VWN/2+FAVWN), sufficient projection data for reconstruction of the first frame of X-ray tomogram by segment data reconstruct processing will have been picked up. When necessary projection data for reconstruction of the first frame of X-ray tomogram have been picked up, the flow will go ahead to step S502.

At step S502, conversion of FAN beam into parallel beam is processed (Fan-Para conversion processing). An outline of the processing to convert FAN beam data into parallel beam data is shown in FIG. 6.

Figures 6A, 6B:
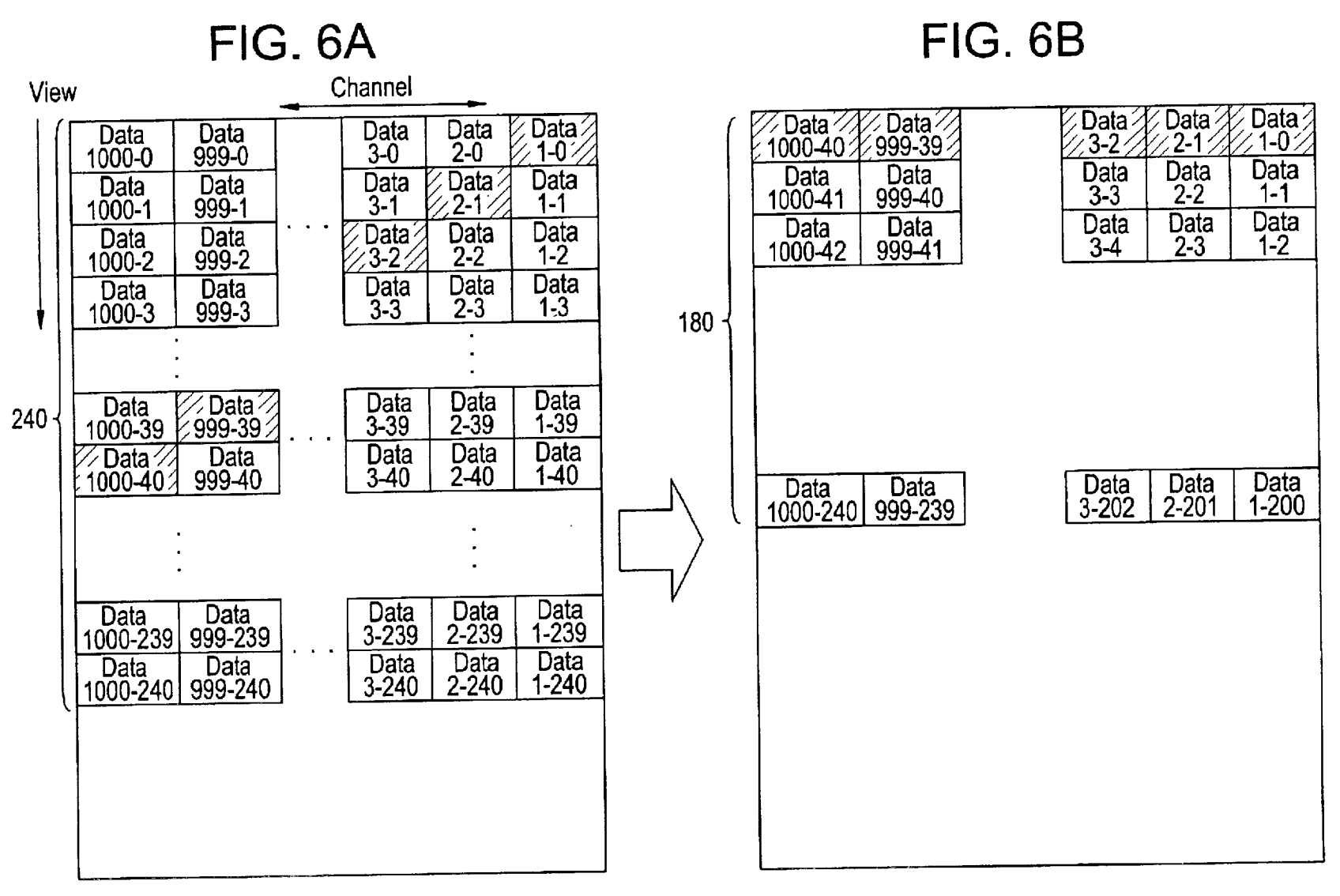

FIG. 6(A) is a profile of collected projection data with the horizontal axis representing channels of the X-ray detector 331 and the vertical axis representing the View direction. The profile is stored in a memory. As illustrated herein, for the sake of convenience of description, the number of channels of the X-ray detector 331 is supposed to be 1000 and one View is supposed to be picked up every time the gantry rotating unit 332 makes a full turn around the subject (VWN=360). Thus it is shown that data 1-0 through data 1000-0 on the first row, for instance, are projection data collected on the channels of the X-ray detector 331 in a View direction of 0 degree, and data 1-1 through data 1000-1 on the second row are projection data collected in a View direction of 1 degree. The fan angle α is supposed to be 60 degrees, and the number of Views matching the fan angle is supposed to be 60 (FAVWN=60) FIG. 6(A) represents picking-up of projection data at 180+α=240 Views.

FIG. 6(B) is a diagram showing that the projection data (fan beam data) shown in FIG. 6(A) have been converted into parallel beam data. In order to obtain parallel beam data at a prescribed angle, data on prescribed projection channels should be extracted from fan beam data in a plurality of View directions. In this example, data on channel 1 (data 1-0) obtained in a View direction of 0 degree and data on channel 2 (data 2-1) obtained in a View direction of 1 degree represent parallel beams differing in penetration path. After this, similarly, data 3-2 and data 1000-40 (hatched data in the diagram) represent beams parallel to each other and differing in penetration path.

Therefore, by rearranging these data in a row as shown in FIG. 6(B), parallel beam data at a prescribed angle can be acquired on that row. Similarly, parallel beam data can also be extracted from data 1-1, 1-2 and so forth (FIG. 6(B) show that 180 sets of parallel beam data have been taken out of projection data in 240 Views). The profile having undergone Fan-Para conversion in this way (i.e., parallel beam data) is transmitted to a back projection processing unit (not shown; one function on the aforementioned diagnosing program) (step S503) to undergo back projection processing (step S405)

<Details of Full Data Reconstruct Processing>

Full data reconstruct processing (Full Recon) means processing to reconstruct an X-ray tomogram on the basis of projection data acquired when a gantry having an X-ray tube and a detector has turned 360 degrees around the subject. Although it takes a longer time to pick up projection data at the time of start of scanning than segment data reconstruct processing does because the quantity of projection data picked up to reconstruct the first frame of X-ray tomogram is greater, it has an advantage over segment data reconstruct processing (Segment Recon) that image quality is superior.

Figure 2A:
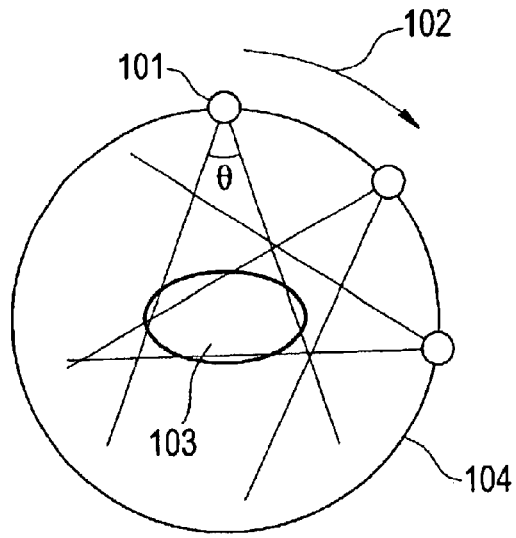
FIG. 2 is conceptual diagrams plainly representing the function of the full data reconstruct processing mode in the usual X-ray CT apparatus.
Figure 2B:
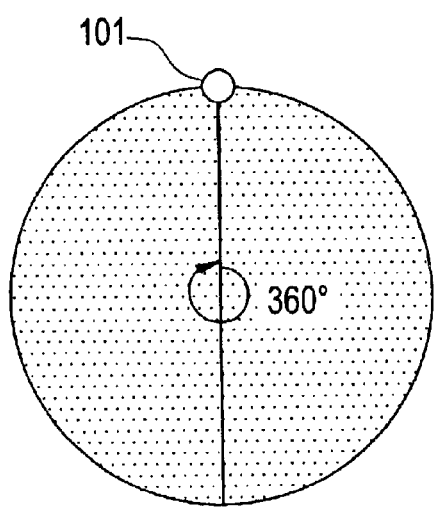
Figure 2C:
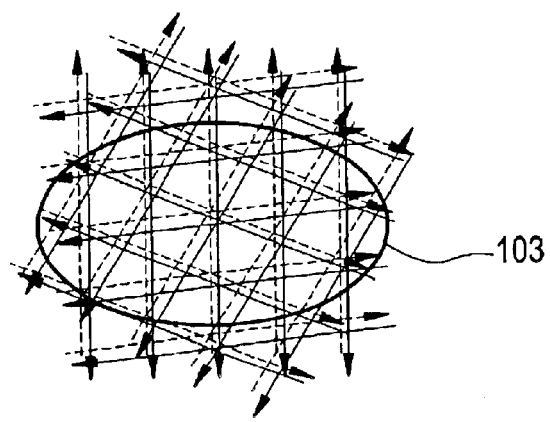

FIG. 2 are conceptual diagrams plainly representing the function of full data reconstruct processing (Full Recon). Since FIG. 2 (A) is the same as FIG. 1(A), its description is dispensed with. FIG. 2(B) illustrates the movement of the X-ray tube during the full data reconstruct processing (Full Recon) until the first frame of X-ray tomogram is reconstructed at the time of start of scanning. Irradiation with X-rays and detection with the detector are started at the position of 0 degree in the diagram and, when the tube has rotated to the position of 360 degrees, the first frame of X-ray tomogram is acquired. FIG. 2(C) shows the penetration paths (indicated by solid line arrows and dotted line arrows in the diagram) of the X-rays penetrating the subject 103 during the rotation of the X-ray tube by 360 degrees. A rotation by 360 degrees gives two parallel beams (the group of solid line arrows and the matching group of dotted line arrows in the reverse diction in FIG. 2(C)) for 180 degrees on each penetration path.

Figure 7:
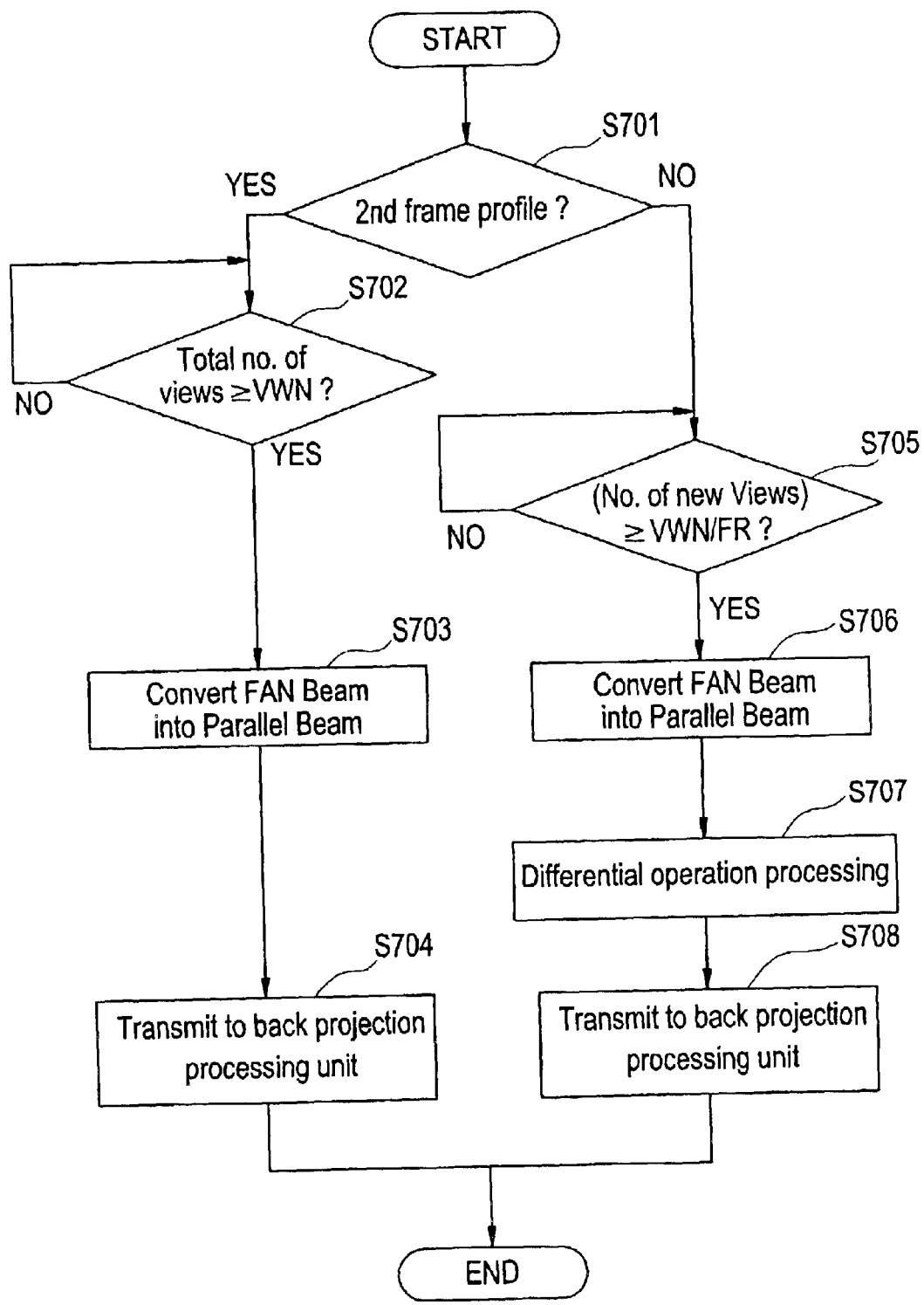
FIG. 7 is a chart showing details of the full data reconstruct processing in the X-ray CT apparatus in the first mode of implementing the invention.

FIG. 7 is a chart showing details of full data reconstruct processing at step S404-2 mentioned above.

At step S701, it is judged whether the frame of X-ray tomogram to be reconstructed is the second frame of X-ray tomogram or the third or any subsequent frame of X-ray tomogram. If it is the second frame of X-ray tomogram, the flow will go ahead to step S702, and waits until the total number of Views after the start of scanning reaches or surpasses VWN. When the total number of Views has reached or surpassed VWN, since that means necessary projection data for reconstruction of one frame of X-ray tomogram by full data reconstruct processing have been picked up, the flow moves ahead to step S703.

At step S703, data equivalent to VWN are subjected to Fan-Para conversion processing (since Fan-Para conversion processing for (VWN/2+FAVWN) after the start of scanning is already done at step S502 actually, Fan-Para conversion processing for the remaining (VWN/2−FAVWN) is done at step S703.

The parallel beam data for 360 degrees acquired at step S703 by Fan-Para conversion processing is transmitted to the back projection processing unit (step S704).

On the other hand, if it is judged at step S701 that the frame of X-ray tomogram to be reconstructed is the third or any subsequent frame of X-ray tomogram, the flow will go ahead to step S705. At step S705, it is judged whether or not the number of new Views not used for the reconstruction of any X-ray tomogram has reached or surpassed VWN/FR. Thus, the rotation of the gantry rotating unit by a predetermined angle of rotation (360/FR) and the new addition of the number of Views of VWN/FR make possible reconstruction of the third and any subsequent frames of X-ray tomogram by full data reconstruct processing. The expression 1/FR refers to the rate of frame updating.

When the necessary number of Views for reconstruction of any new X-ray tomogram has been picked up at step S705, the flow goes ahead to step S706 to subject the newly picked-up projection data to Fan-Para conversion processing. As a result, necessary parallel beam data for reconstructing the new X-ray tomogram are acquired.

Figure 8:
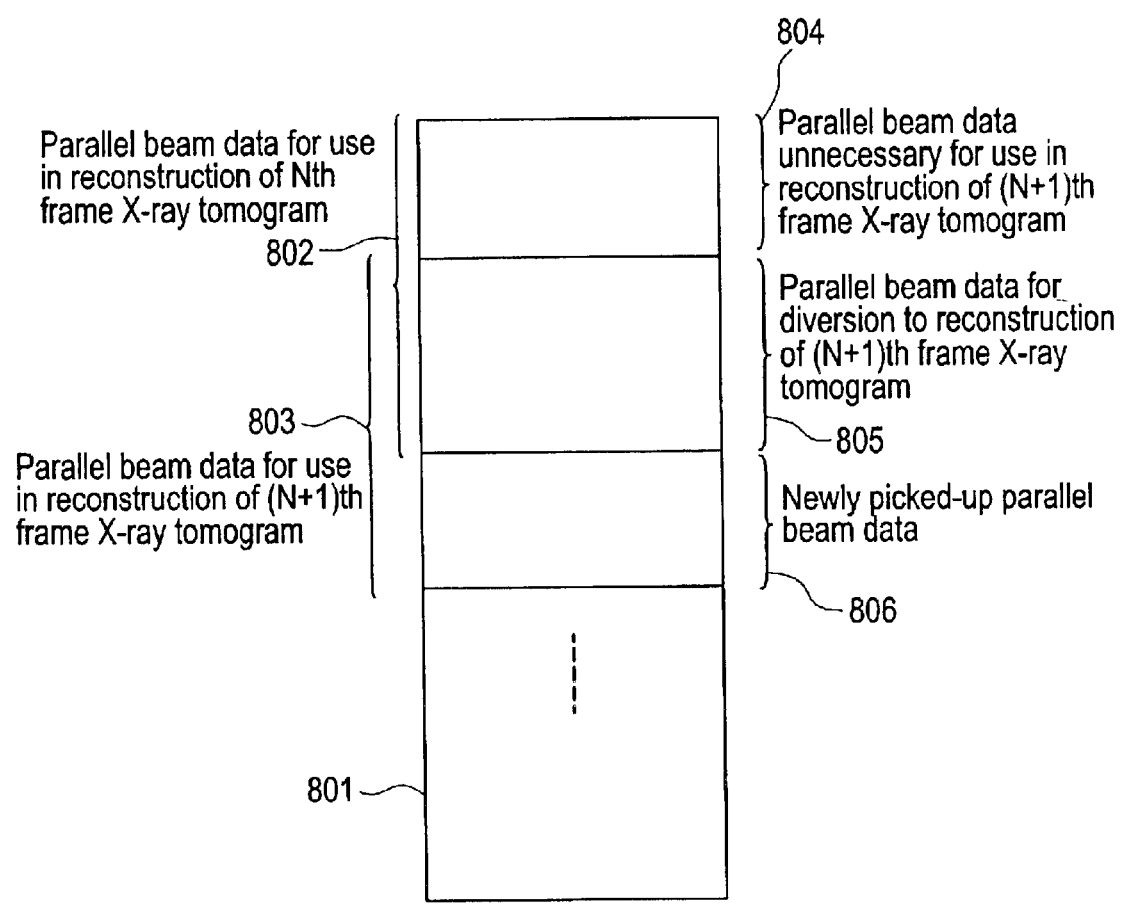
FIG. 8 is a chart showing an outline of the differential operation processing in the X-ray CT apparatus in the first mode of implementing the invention.

Next at step S707, differential operation processing is performed. FIG. 8 is a diagram plainly representing the contents of the differential operation processing. Reference numeral 801 denotes parallel beam data having undergone Fan-Para conversion processing. The area denoted by 802 represents parallel beam data for use in reconstructing the Nth frame of (N is any value not smaller than 2) X-ray tomogram, and that by 803 represents parallel beam data for use in reconstructing the (N+1) frame of X-ray tomogram. In reconstructing the (N+1) frame of X-ray tomogram, in addition to diverting the parallel beam data in the area denoted by 805 out of the parallel beam data 802 used for reconstructing the Nth frame of X-ray tomogram, the parallel beam data in the area denoted by 804 (parallel beam data unnecessary for reconstructing the (N+1) frame of X-ray tomogram) can be deleted, and the parallel beam data in the area denoted by 806 (newly picked-up parallel beam data) can be added. Thus, parallel beam data resulting from the subtraction of the parallel beam data in the area denoted by 804 from the parallel beam data in the area denoted by 806 can bet transmitted to the back projection processing unit.

Thus, the differential operation processing means processing to calculate the difference of the new parallel beam data (parallel beam data for VWN/FR) and the parallel beam data used for reconstruction of the x-ray tomogram of the frame before) from the earlier picked-up parallel beam data VWN/FR. This differential operation processing can serve to reduce the processing load in back projection processing.

Thus, since sets of parallel beam data in the area denoted by 802 are superposed over each other in the back projection processing, it is necessary, in updating the X-ray tomogram, to perform processing to superpose a new set of parallel beam data denoted by 806 and delete an earlier picked-up set of parallel beam data denoted by 804 (both addition processing and subtraction processing should be performed). However, if the difference between the new parallel beam data denoted by 806 and the earlier picked-up parallel beam data denoted by 804is calculated by the differential operation processing in advance and transmitted to the back projection processing unit, only addition needs to be processed in back projection processing, resulting in a reduced processing load in the back projection processing.

Referring back to FIG. 7, the parallel beam data subjected the differential operation processing are transmitted to the back projection processing unit (step S708), and undergo back projection processing (step S405).

Next will be described the flow of X-ray tomogram reconstruction in the Smart View mode with reference to the time chart of FIG. 9.

As stated above, the number of Views needed for preparing the first frame ($N_{profile}$) is, with the number of Views needed for a full turn of the gantry being represented by VWN, the number of Views of Fan Angle by FAVWN, and the rate of frame updating by 1/FR:

$$N_{profile} = VWN/2 + FAVWN$$

Figure 9:
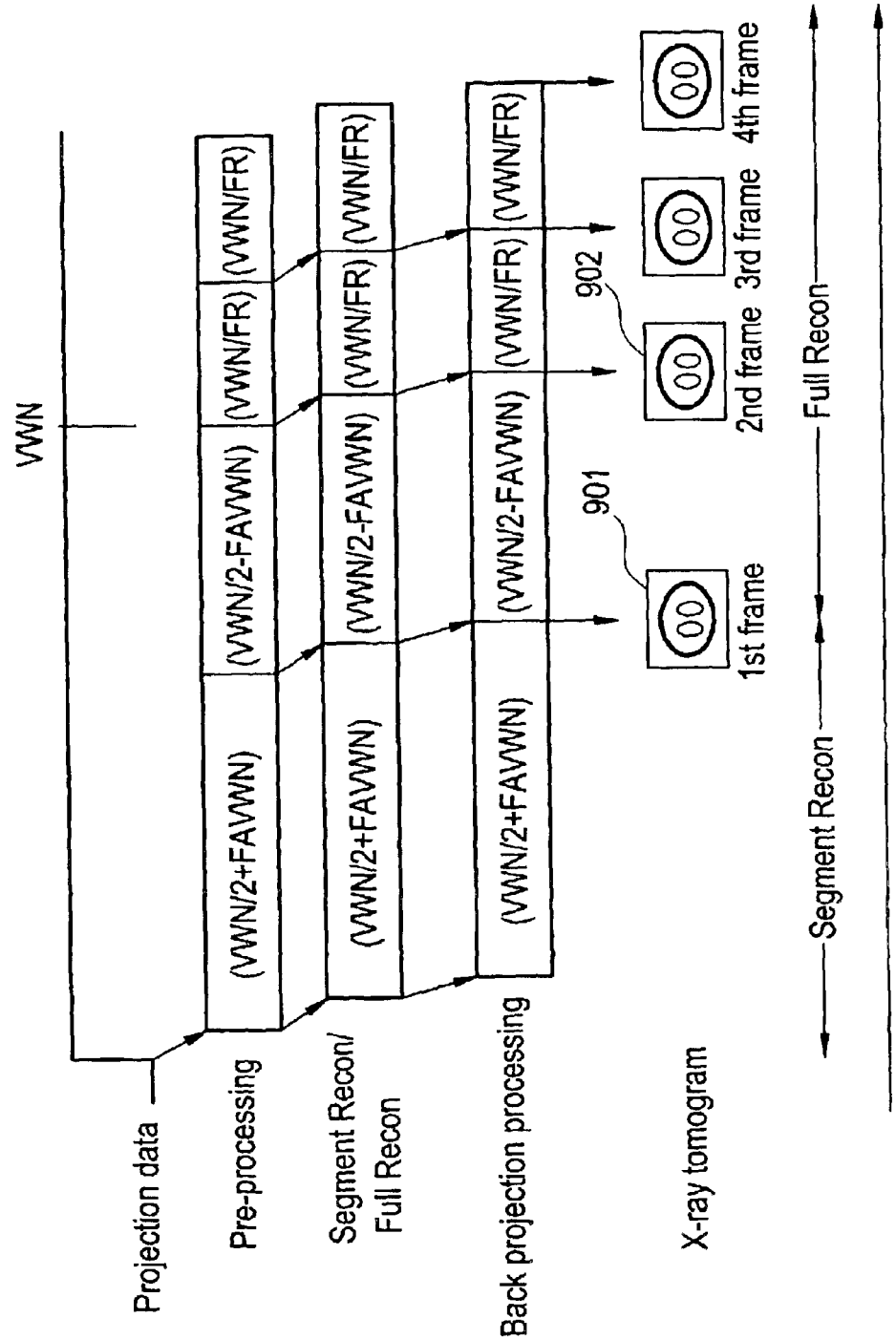
FIG. 9 is a chart showing the flow of X-ray tomogram reconstruct processing in the X-ray CT apparatus in the first mode of implementing the invention.

Therefore, the first frame of X-ray tomogram is displayed by picking up and reconstructing the number of Views for (VWN/2+FAVWN) (901 in FIG. 9).

Next, the second frame of X-ray tomogram is reconstructed by full data reconstruct processing as the total number of Views becomes VWN (902 in FIG. 9). After this, it becomes possible to reconstruct X-ray tomograms without using the number of Views for a full turn of the gantry (i.e., Full Recon). As a result, from the second frame onward, X-ray tomograms of high image quality, free from tangent artifacts or artifacts dependent on the tube-detector angles, can be acquired. Once the number of Views reaches VWN, from then onward, if the rate of frame updating remains constant, the load of processing in the differential operation processing, whether in Segment Recon or in Full Recon, will be the same (in this particular case, Views of VWN/FR are added and as many Views are deleted), and accordingly there will be no difference in the real-time capability. On the other hand, when Full Recon is used as referred to above, as the number of Views used in X-ray tomogram reconstruction is great, there is the benefit that X-ray tomograms of high image quality can be acquired.

As described above, in performing reconstruct processing of X-ray tomograms in the real-time display mode, while keeping short the length of time until the reconstruction of the first frame of X-ray tomogram by counting the number of frames and changing over between the use of segment data reconstruct processing or that of full data reconstruct processing according to the number of frames counted, image quality improvement of the second and subsequent frames of X-ray tomogram and artifact reduction can be achieved.

(Second Mode of Implementation)

In the first mode of implementation described above, the processing method according to the invention under the present application is applied to an X-ray CT apparatus for performing Fan-Para conversion. However, the invention under the application can also be applied to an X-ray CT apparatus which does not perform Fan-Para conversion processing. In view of this point, referring to this mode of implementation, a case of applying the invention to an X-ray CT apparatus which does not perform Fan-Para conversion processing will be described in detail below.

<X-ray CT Apparatus not Performing Fan-Para Conversion>

An X-ray CT apparatus not performing Fan-Para conversion means an X-ray CT apparatus of a system of directly reconstructing fan beam data, and has an advantage over an X-ray CT apparatus which does perform Fan-Para conversion that the X-ray detector can be simplified. Thus, an X-ray CT apparatus performing Fan-Para conversion, in order to pick up projection data for one View, it is necessary to divide the X-ray detector into 16 parts and to cause each part to pick up data with timing lags from others. This entails a problem of a higher X-ray detector cost.

By contrast, where Fan-Para conversion is not performed, it is possible for the X-ray detector to collectively pick up one View.

On the other hand, an X-ray CT apparatus not performing Fan-Para conversion has its own disadvantage that, when Segment Recon is used, requires processing known as segment weighting (to be detailed afterwards), resulting in an increased processing load on the X-ray CT apparatus. This gives rise to a new problem that, where segment data reconstruct processing is performed in the real-time display mode as according to the prior art, the increased processing load invites a deterioration in the real-time capability as the number of frames increases on top of poor image quality.

By using the invention under the present application by contrast, it is possible not to let the real-time capability deteriorate even if the number of frames increases while keeping short the length of time until the reconstruction of the first frame of X-ray tomogram, and moreover to improve the image quality over the prior art.

<Details of Reconstruct Processing and of Segment Data Reconstruct processing>

Figure 10:
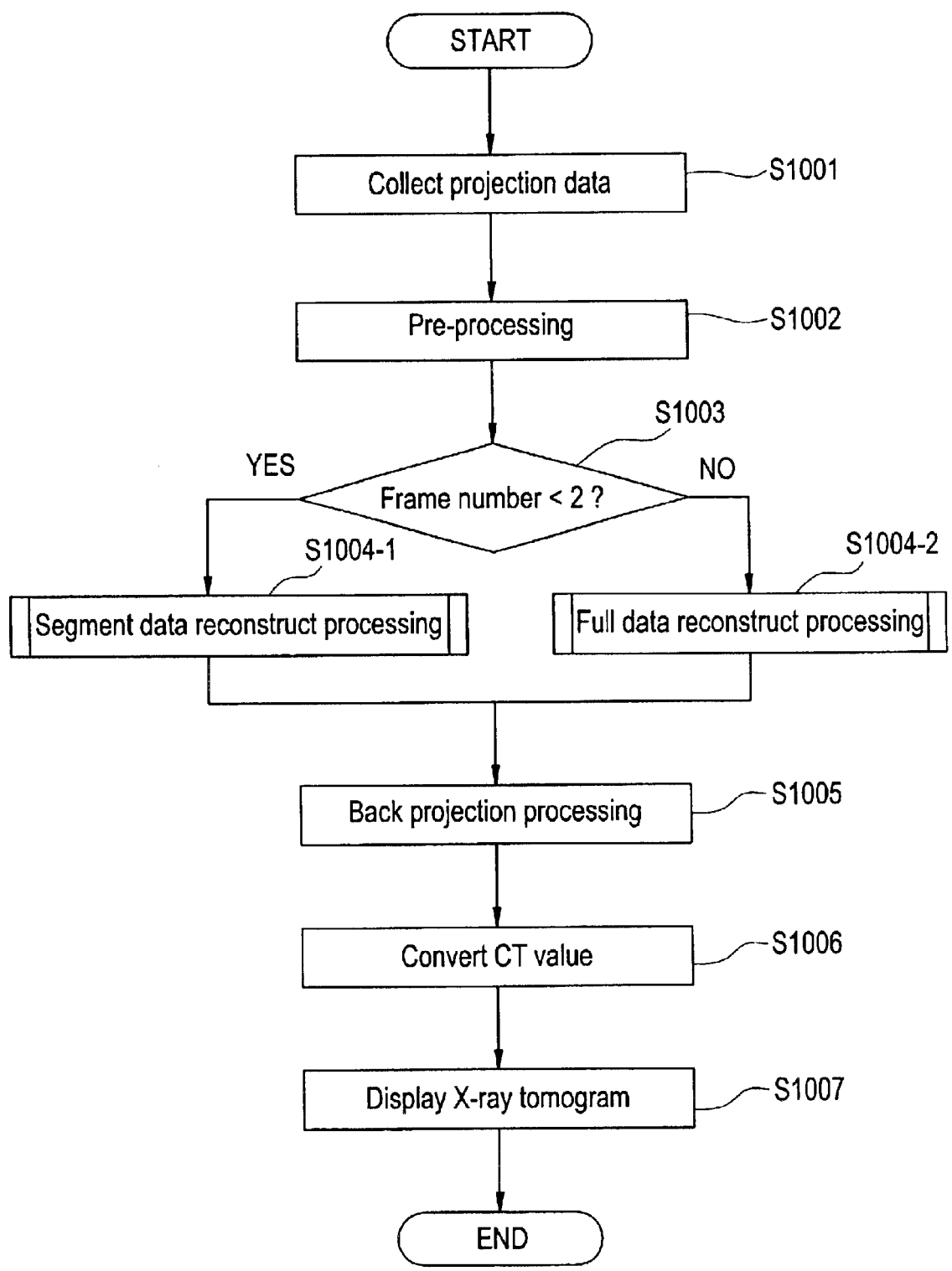
FIG. 10 is a chart showing the flow of processing to reconstruct X-ray tomograms in the diagnosing program stored in the X-ray CT apparatus in the second mode of implementing the invention.

FIG. 10 is a chart showing the flow of processing to reconstruct X-ray tomograms in the diagnosing program stored in the X-ray CT apparatus in the second mode of implementing the present invention. As it is similar to FIG. 4, further description is dispensed with.

Figure 11:
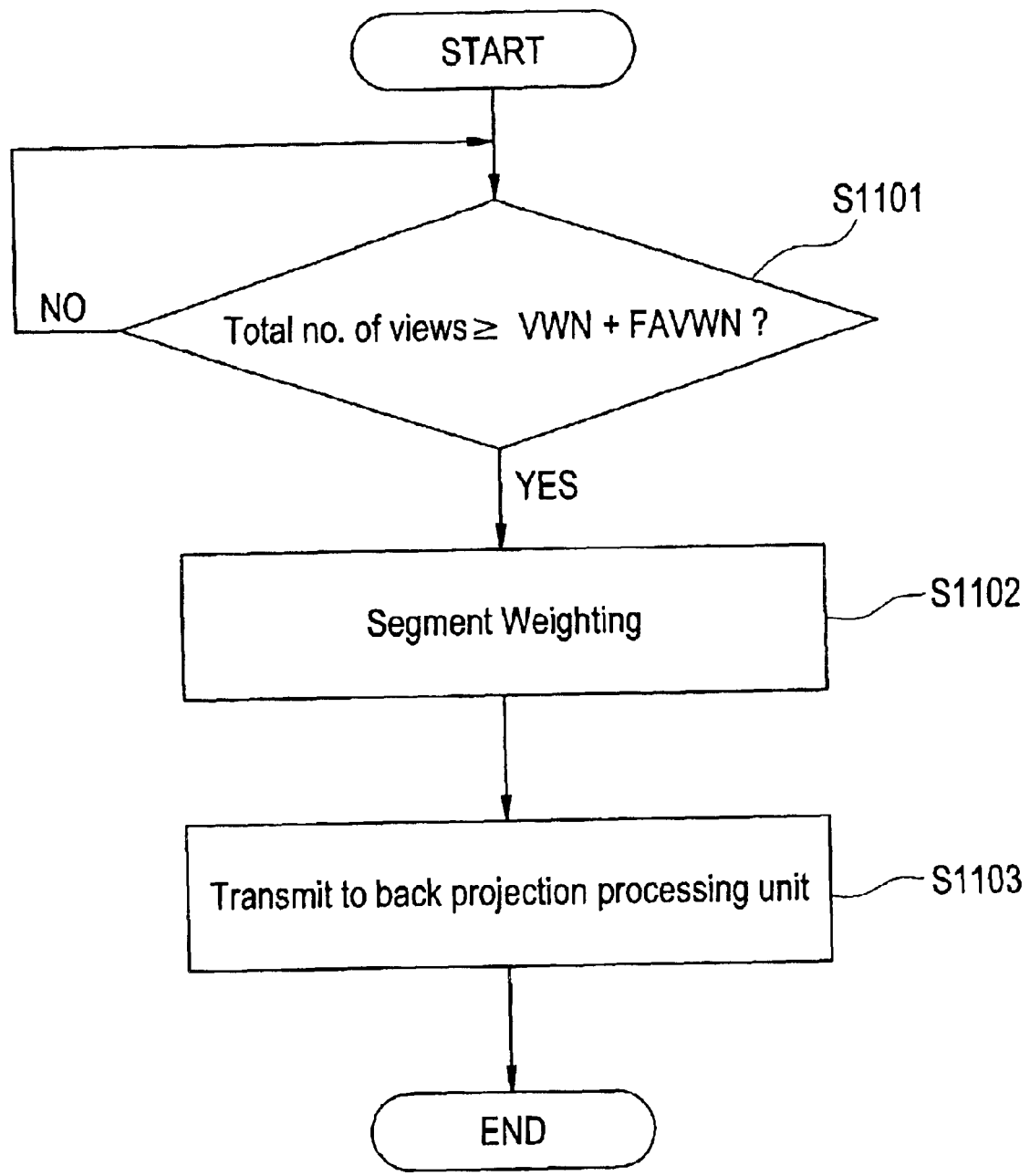
FIG. 11 is a chart showing details of the segment data reconstruct processing in the X-ray CT apparatus in the second mode of implementing the invention.

FIG. 11 is a flow chart showing details of the segment data reconstruct processing (step S1004-1) shown in FIG. 10.

At step S1101, the total number of Views since the start of scanning is counted. If the total number of Views since the start of scanning reaches (VWN/2+FAVWN), necessary projection data for reconstructing the first frame of X-ray tomogram by segment data reconstruct processing will have been picked up. When the necessary projection data for reconstructing the first frame of X-ray tomogram have been picked up, the flow goes ahead to step S1102.

Figure 12:
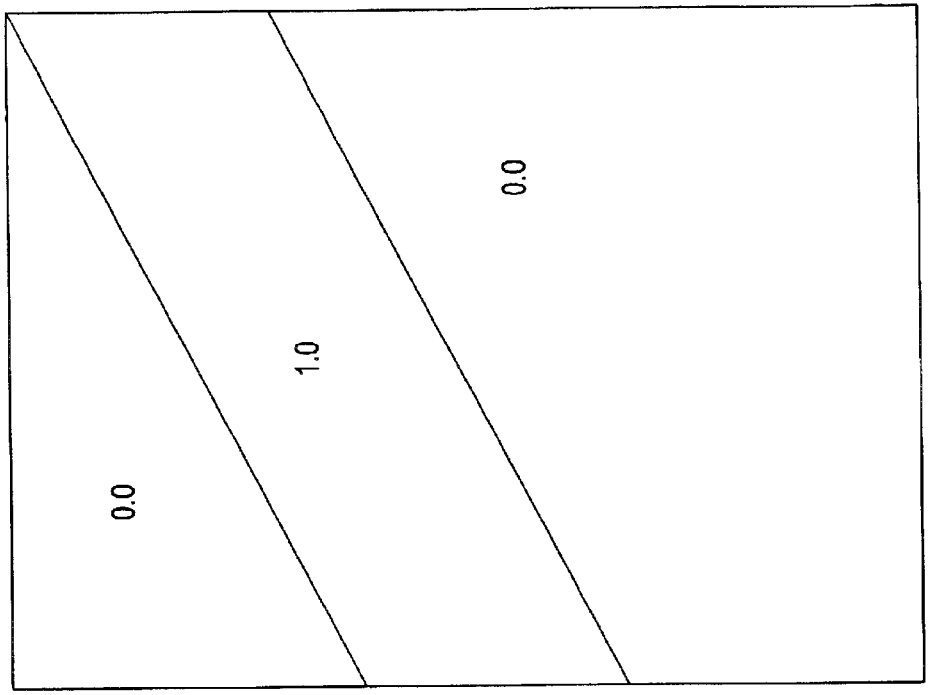
FIG. 12 is charts showing an outline of the Segment Weighting in the X-ray CT apparatus in the second mode of implementing the invention.

At step S1102, the picked-up projection data are subjected to segment weighting. The segment weighting will now be described with reference to FIG. 12. FIG. 12(A) is a profile of collected projection data with the horizontal axis representing channels of the X-ray detector and the vertical axis representing the View direction. The profile is stored in a memory. As already stated regarding the first mode of implementation, for reconstructing a tomogram, projection data for(180+α) degrees shown below the data in the hatched part of the diagram, such as data 1-0, data 2-1 and so forth (projection data constituting parallel beams) (in this mode of implementation, too, as in the first mode of implementation, supposing FR=360, α=60 and FAVWN=60, projection data for 240 degrees) are required, but other projection data are unnecessary for the reconstruction of that particular frame of tomogram.

Therefore, to delete such unnecessary projection data, the picked-up projection data are multiplied by an appropriate one of the coefficients in the segment weighting table shown in FIG. 12(B). Thus, the part of projection data to be used for the reconstruction of the particular frame of tomogram is multiplied by a coefficient 1.0, and the part of projection data not to be used, by a coefficient 0.0 (although two kinds of coefficient, 1.0 and 0.0, are shown in this example of segment weighting table, the choice of coefficients is not limited to this, but in the boundary part between coefficients 1.0 and 0.0, some intermediate value between them can be used as well).

Referring back to FIG. 11, the profile subjected to segment weighting is transmitted to the back projection processing unit (step S1103), and undergoes back projection processing.

<Details of Full Data Reconstruct Processing>

Figure 13:
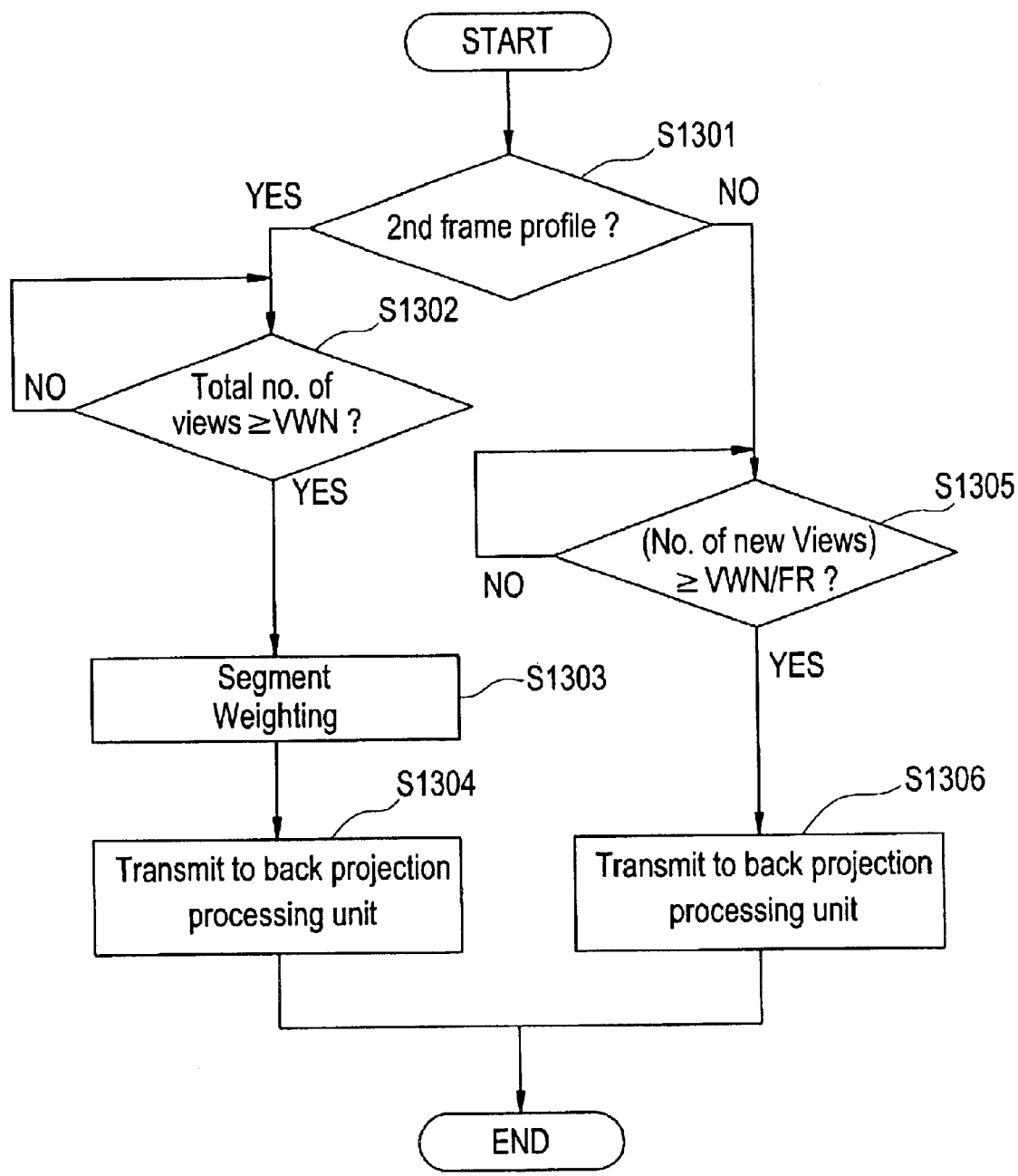
FIG. 13 is a chart showing details of the full data reconstruct processing in the X-ray CT apparatus in the second mode of implementing the invention.

FIG. 13 is a chart showing details of the full data reconstruct processing at step S1004-2 referred to above.

At step S1301, it is judged whether the frame to undergo X-ray tomogram reconstruction is frame of X-ray tomogram or the third or any subsequent frame of X-ray tomogram. If it is the second frame of X-ray tomogram, the flow will go ahead to step S1302, and waits until the total number of Views after the start of scanning reaches or surpasses VWN. When the total number of Views has reached or surpassed VWN, since that means necessary projection data for reconstruction of one frame of X-ray tomogram by full data reconstruct processing have been picked up, the flow moves ahead to step S1303.

At step S1303, segment weighting is processed. FIG. 14 show an example of segment weighting table for use in reconstructing the second frame of X-ray tomogram by full data reconstruct processing. In full data reconstruct processing, unlike in segment data reconstruct processing, all the Views are used equally, the segment weighting table shows 1.0 (i.e., no segment weighting needs to be processed).

The fan beam data subjected to segment weighting are transmitted to the back projection processing unit (step S1304) to undergo back projection processing.

On the other hand, if it is judged at step S1301 that the frame of X-ray tomogram to be reconstructed is the third or any subsequent frame of X-ray tomogram, the flow will go ahead to step S1305. At step S1305, it is judged whether or not the number of new Views not used for the reconstruction of any X-ray tomogram has reached or surpassed VWN/FR. Thus, the rotation of the gantry rotating unit by a predetermined angle of rotation (360/FR) and the new addition of the number of Views of VWN/FR make possible X-ray tomogram reconstruction by full data reconstruct processing. The expression 1/FR refers to the rate of frame updating.

Next will be described the flow of X-ray tomogram reconstruction in the Smart View mode with reference to the time chart of FIG. 15.

As stated above, the number of Views needed for preparing the first frame ($N_{profile}$) is, with the number of Views needed for a full turn of the gantry being represented by VWN, the number of Views matching the fan angle by FAVWN, and the rate of frame updating by 1/FR:

$$N_{profile}=VWN/2+FAVWN$$

Figure 15:
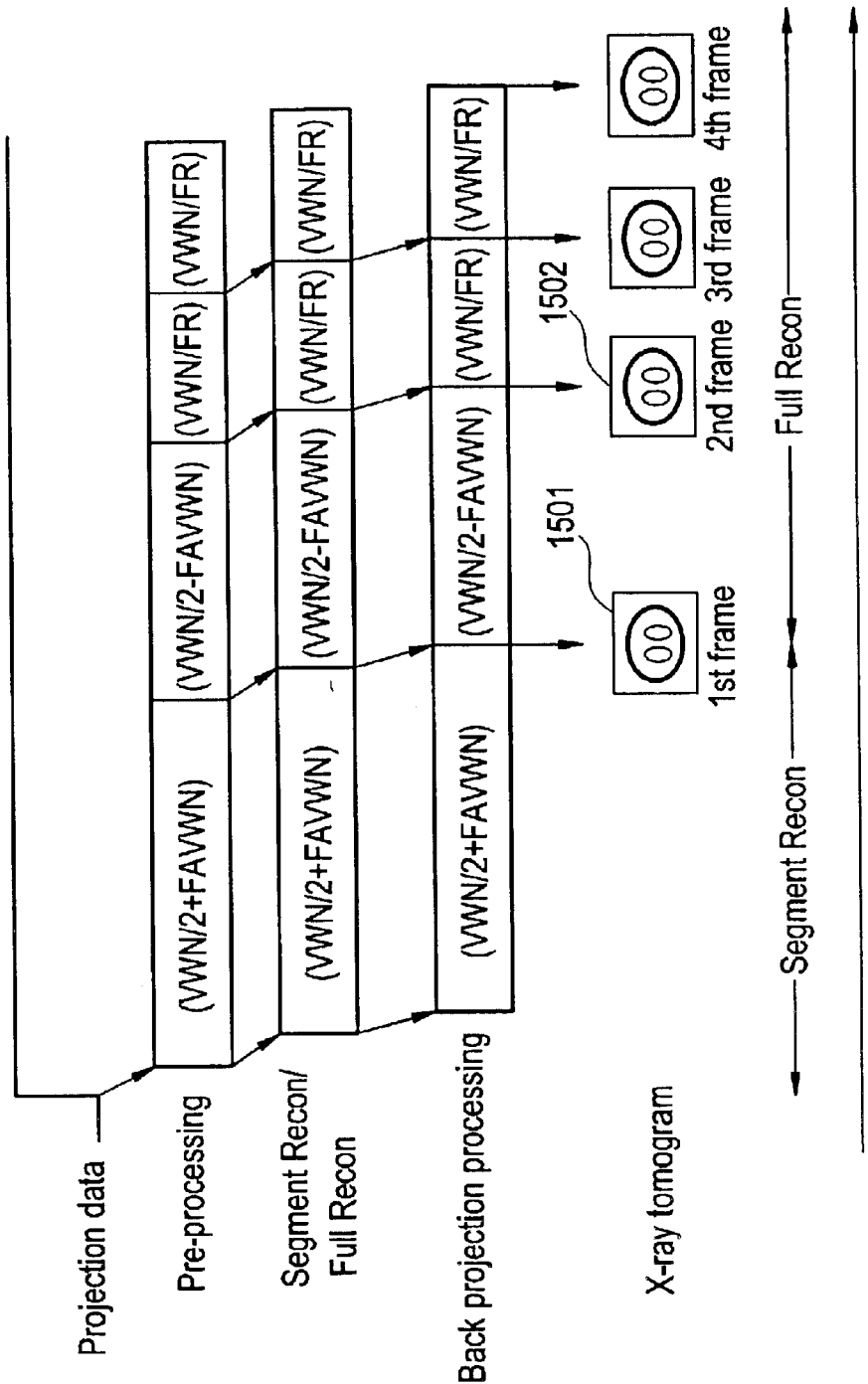
FIG. 15 is a chart showing the flow of X-ray tomogram reconstruct processing in the X-ray CT apparatus in the second mode of implementing the invention.

Therefore, the first frame of X-ray tomogram is displayed by picking up and reconstructing the number of Views for (VWN/2+FAVWN) (1501 in FIG. 15).

Next, the second frame of X-ray tomogram is reconstructed by full data reconstruct processing as the total number of Views becomes VWN (1502 in FIG. 15). After this, it becomes possible to reconstruct X-ray tomograms without using the number of Views for a full turn of the gantry (i.e., Full Recon). As a result, from the second frame onward, X-ray tomograms of high image quality can be acquired. Incidentally, as stated above, in X-ray tomogram reconstruction by Full Recon, Segment Weighting can be dispensed with, but all the projection data are used for reconstruction. As a result, the load of processing on the X-ray CT apparatus can be reduced and, unlike in Segment Recon, there is no deterioration in the real-time capability with an increase in the number of frames. On the other hand, when Full Recon is used as referred to above, as the number of Views used in X-ray tomogram reconstruction is great, there is the benefit that X-ray tomograms of high image quality can be acquired.

Thus, it has been demonstrated that the data processing method according to the invention is applicable not only to X-ray CT apparatuses performing Fan-Para conversion but only X-ray CT apparatuses not performing Fan-Para conversion. Moreover, the method makes it possible to provide, while enjoying the benefit of reducing the X-ray detector cost provided by X-ray CT apparatuses using Fan-Para conversion, an additional benefit of solving the problem encountered in using Segment Recon in the Smart Recon mode, inherent in X-ray CT apparatuses not performing Fan-Para conversion.

Many widely different embodiments of the invention may be configured without departing from the spirit and the scope of the present invention. It should be understood that the present invention is not limited to the specific embodiments described in the specification, except as defined in the appended claims.

What is claimed is:

1. An X-ray CT apparatus having a rotary unit for causing an X-ray source and an X-ray detector for detecting X-rays from the X-ray source to rotate integrally around a subject, comprising:
   a full data reconstructing device for reconstructing tomograms on the basis of penetrating X-ray data of each view detected during a full turn around said subject;
   a segment data reconstructing device for reconstructing tomograms on the basis of penetrating X-ray data of each view detected during rotating at a prescribed angle less than a full turn around said subject; and
   a change-over device for counting the tomograms reconstructed after the start of scanning, and changing over between said full data reconstructing device and segment data reconstructing device according to the count.

2. The X-ray CT apparatus of claim 1, wherein said full data reconstructing device and said segment data reconstructing device are further provided with conversion processing device for converting fan beam data, which are penetrating X-ray data for each detected view, into parallel beam data.

3. The X-ray CT apparatus of claim 1, wherein said prescribed rotating angle is an angle adequate for picking up a first number of views, which is the necessary number of views for extracting said parallel beam data for 180 degrees on the basis of said detected penetrating X-ray data.

4. The X-ray CT apparatus of claim 1, wherein after the start of scanning the first tomogram is reconstructed by using said segment data reconstructing device, and then said change-over device changes over to said full data reconstructing device to reconstruct the second and subsequent tomograms consecutively.

5. The X-ray CT apparatus of claim 1, wherein said segment data reconstructing device counts the number of views in which penetrating X-ray data have been detected after the start of scanning and, when said first number of views is surpassed, reconstructs the first tomogram.

6. The X-ray CT apparatus of claim 1, wherein said full data reconstructing device counts the number of views in which penetrating X-ray data have been detected after the start of scanning and, when a second number of views which is the number of views detected during a full turn around said subject is surpassed, reconstructs the second tomogram on the basis of said full data reconstructing device.

7. The X-ray CT apparatus of claim 1, wherein said full data reconstructing device, in reconstructing the third and subsequent tomograms, reconstructs a new tomogram when reaching a number of views matching a predetermined rotating angle.

8. The X-ray CT apparatus of claim 1, wherein said full data reconstructing device is further provided with a differential operation processing device which, in reconstructing the third and subsequent tomograms, computes the difference between parallel beam data extracted on the basis of newly detected penetrating X-ray data and the parallel beam data used for reconstructing the immediately preceding tomogram.

9. The X-ray CT apparatus of claim 1, wherein said full data reconstructing device and said segment data reconstructing device directly reconstruct tomograms by using fan beam data, which are penetrating X-ray data for each detected view.

10. The X-ray CT apparatus of claim 1, wherein said prescribed rotating angle is an angle adequate for picking up a first number of views, which is the necessary number of views for extracting said parallel beam data for 180 degrees on the basis of said detected penetrating X-ray data.

11. The X-ray CT apparatus of claim 1, wherein said segment data reconstructing device is further provided with a device for performing weighting to extract parallel beam data with respect to said detected fan beam data.

12. The X-ray CT apparatus of claim 1, wherein after the start of scanning the first tomogram is reconstructed by using said segment data reconstructing device, and then said change-over device changes over to said full data reconstructing device to reconstruct the second and subsequent tomograms consecutively.

13. The X-ray CT apparatus of claim 1, wherein said segment data reconstructing device counts the number of views in which penetrating X-ray data have been detected after the start of scanning and, when said first number of views is surpassed, reconstructs the first tomogram.

14. The X-ray CT apparatus of claim 1, wherein said full data reconstructing device counts the number of views in which penetrating X-ray data have been detected after the start of scanning and, when a second number of views which is the number of views detected during a full turn around said subject is surpassed, reconstructs the second tomogram on the basis of said full data reconstructing device.

15. The X-ray CT apparatus of claim 1, wherein said full data reconstructing device, in reconstructing the third and subsequent tomograms, reconstructs a new tomogram when reaching a number of views matching a predetermined rotating angle.

16. A processing method for use in an X-ray CT apparatus having a rotary unit for causing an X-ray source and an X-ray detector for detecting X-rays from the X-ray source to rotate integrally around a subject, comprising the steps of:
   a full data reconstructing step of reconstructing tomograms on the basis of penetrating X-ray data of each view detected during a full turn around said subject;
   a segment data reconstructing step of reconstructing tomograms on the basis of penetrating X-ray data of each view detected during rotating at a prescribed angle less than a full turn around said subject; and
   a change-over step of counting the tomograms reconstructed after the start of scanning, and changing over between said full data reconstructing step and segment data reconstructing step according to the count.

17. The processing method of claim 16, wherein said full data reconstructing step and said segment data reconstructing step are further provided with conversion processing steps for converting fan beam data, which are penetrating X-ray data for each detected view, into parallel beam data.

18. The processing method of claim 16, wherein said prescribed rotating angle is an angle adequate for picking up a first number of views, which is the necessary number of views for extracting said parallel beam data for 180 degrees on the basis of said detected penetrating X-ray data.

19. The processing method of claim 16, wherein after the start of scanning the first tomogram is reconstructed by using said segment data reconstructing step, and then change-over to said full data reconstructing step is performed at said change-over step to reconstruct the second and subsequent tomograms consecutively.

20. The processing method of claim 16, wherein the number of views in which penetrating X-ray data have been detected after the start of scanning is counted at said segment data reconstructing step and, when said first number of views is surpassed, the first tomogram is reconstructed.

21. The processing method of claim 16, wherein the number of views in which penetrating X-ray data have been detected after the start of scanning is counted at said full data reconstructing step and, when a second number of views which is the number of views detected during a full turn around said subject is surpassed, the second tomogram is reconstructed on the basis of said full data reconstructing step.

22. The processing method of claim 16, wherein at said full data reconstructing step, in reconstructing the third and subsequent tomograms, a new tomogram is reconstructed when reaching a number of views matching a predetermined rotating angle.

23. The processing method of claim 16, wherein said full data reconstructing step is further provided with a differential operation processing step at which, in reconstructing the third and subsequent tomograms, the difference between parallel beam data extracted on the basis of newly detected penetrating X-ray data and the parallel beam data used for reconstructing the immediately preceding tomogram is computed.

24. The processing method of claim 16, wherein at said full data reconstructing step and said segment data reconstructing step tomograms are directly reconstructed by using fan beam data, which are penetrating X-ray data for each detected view.

25. The processing method of claim 16, wherein said prescribed rotating angle is an angle adequate for picking up a first number of views, which is the necessary number of views for extracting said parallel beam data for 180 degrees on the basis of said detected penetrating X-ray data.

26. The processing method of claim 16, wherein said segment data reconstructing step is further provided with a step of performing weighting to extract parallel beam data with respect to said detected fan beam data.

27. The processing method of claim 16, wherein after the start of scanning the first tomogram is reconstructed by using said segment data reconstructing step, and then at said change-over step change-over to said full data reconstructing step is performed to reconstruct the second and subsequent tomograms consecutively.

28. The processing method of claim 16, wherein at said segment data reconstructing step the number of views in which penetrating X-ray data have been detected after the start of scanning are counted and, when said first number of views is surpassed, the first tomogram is reconstructed.

29. The processing method of claim 16, wherein at said full data reconstructing step the number of views in which penetrating X-ray data have been detected after the start of scanning is counted and, when a second number of views which is the number of views detected during a full turn around said subject is surpassed, the second tomogram is reconstructed on the basis of said full data reconstructing step.

30. The processing method of claim 16, wherein at said full data reconstructing step, in reconstructing the third and subsequent tomograms, a new tomogram is reconstructed when reaching a number of views matching a predetermined rotating angle.

31. A recording medium storing a control program for executing with a computer a processing method for use in the X-ray CT apparatus of claim 16.

* * * * *